US005560353A

United States Patent [19]

Willemot et al.

[11] Patent Number: 5,560,353
[45] Date of Patent: Oct. 1, 1996

[54] EQUIPMENT AND PROCESS FOR SUPPLYING DOSES OF AT LEAST ONE GAS TO THE RESPIRATORY TRACTS OF A USER

[75] Inventors: Jean-Marie Willemot, Sceaux; Daniel Desforges, Santeuil, both of France

[73] Assignee: TAEMA, Antony, France

[21] Appl. No.: 350,018

[22] Filed: Nov. 29, 1994

Related U.S. Application Data

[63] Continuation of Ser. No. 95,709, Jul. 23, 1993, abandoned.

[30] Foreign Application Priority Data

Jul. 23, 1992 [FR] France .................................. 92 09075

[51] Int. Cl.$^{6}$ .................................................. A61M 16/00

[52] U.S. Cl. ............................... 128/204.21; 128/204.23; 128/203.11; 128/203.12; 128/203.27

[58] Field of Search ......................... 128/204.21, 204.23, 128/204.26, 203.11, 203.12, 200.23, 203.16, 203.17, 203.26, 203.27

[56] References Cited

U.S. PATENT DOCUMENTS

| | | | |
|---|---|---|---|
| 4,106,503 | 8/1978 | Rosenthal et al. | 128/200.14 |
| 4,109,656 | 8/1978 | Goethel et al. | 128/203.15 |
| 4,279,250 | 7/1981 | Valenta | 128/200.14 |
| 4,336,590 | 6/1982 | Jacq et al. | 364/418 |
| 4,345,612 | 8/1982 | Koni et al. | 137/101.19 |
| 4,464,172 | 8/1984 | Lichtenstein | 604/65 |
| 4,681,099 | 7/1987 | Sato et al. | 128/204.23 |
| 4,934,358 | 6/1990 | Nilsson et al. | 128/200.23 |
| 4,951,661 | 8/1990 | Sladek | 128/202.27 |
| 4,971,049 | 11/1990 | Rotariu et al. | 128/204.21 |
| 4,984,158 | 1/1991 | Hillsman | 364/413.04 |
| 5,020,527 | 6/1991 | Dessertine | 128/200.23 |
| 5,104,374 | 4/1992 | Bishko et al. | 604/31 |
| 5,134,995 | 8/1992 | Gruenke et al. | 128/204.23 |
| 5,156,776 | 10/1992 | Loedding et al. | 128/203.12 |
| 5,165,397 | 11/1992 | Arp | 128/204.21 |
| 5,237,987 | 8/1993 | Anderson et al. | 128/204.18 |
| 5,284,133 | 2/1994 | Burns et al. | 128/200.23 |
| 5,392,768 | 2/1995 | Johansson et al. | 128/200.14 |

FOREIGN PATENT DOCUMENTS

| | | |
|---|---|---|
| 0188071 | 7/1986 | European Pat. Off. . |
| 0483556 | 6/1992 | European Pat. Off. . |
| 2598918 | 11/1987 | France . |
| WO9014121 | 11/1990 | WIPO . |
| WO9006336 | 5/1991 | WIPO . |

*Primary Examiner*—V. Millin
*Assistant Examiner*—William J. Deane, Jr.
*Attorney, Agent, or Firm*—Browdy and Neimark

[57] ABSTRACT

A system supplies discrete puffs of gas, containing particles of an active product, to a patient's respiratory tract. A nebulizer containing the particles is in a gas circuit supplying gas to the user. A gas flow control delivers a metered amount of the gas to the nebulizer and to the user in each puff. Breath phases of the patient are sensed for initiating each of the puffs at the correct point in the breath cycle, and for counting the puffs. The sequence of puffs is programmably controlled and the puffs in a predetermined sequence according to a puff sequence program. The puff sequence program includes a maximum number of puffs, times and dates of treatment, etc. A transportable memory storage unit, such as a chip or a magnetic card, is used for transporting the puff sequence program to the controller, which includes a reader/writer to accept the puff sequence program from the memory storage unit, and also for recording the times and amounts actually used by the patient on the memory storage unit. A physician's programing station is used for for entering the puff sequence program onto the memory storage unit and reading back the treatments taken by the patient.

13 Claims, 1 Drawing Sheet

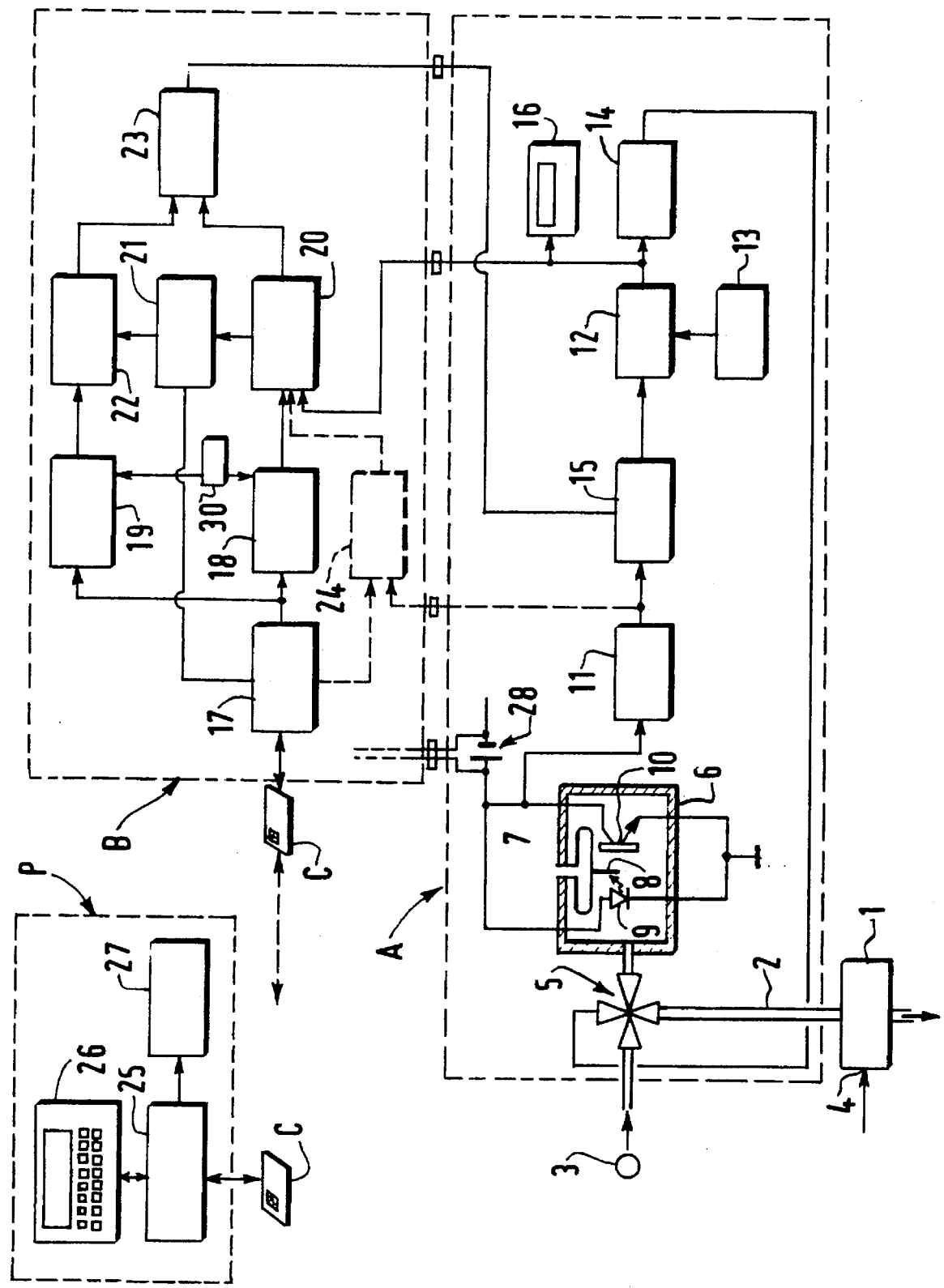

EQUIPMENT AND PROCESS FOR SUPPLYING DOSES OF AT LEAST ONE GAS TO THE RESPIRATORY TRACTS OF A USER

This application is a continuation of application Ser. No. 08/095,709, filed Jul. 23, 1993 now abandoned.

BACKGROUND OF INVENTION

1. Field of the Invention

The present invention concerns equipments for supplying to the respiratory tracts of a user doses of at least one gas containing particles of at least one active product, comprising, in series, in a gas circuit between a source of gas and the respiratory tracts, a gas distribution valve and a nebulizer, the valve being controlled by means of a control device comprising a sensor which is responsive to the inhalation phases of the user.

2. Description of Prior Art

Respiratory aid to patients as well as treatments by means of aerosols take an increasingly important place in pulmonary pathology. The equipments which are presently available are generally specific to certain treatments, and for this reason they have a poor flexibility of adaptation for various uses and do not guarantee a sufficient level of safety in the absence of a practitioner, for example in paediatrics.

SUMMARY OF INVENTION

It is an object of the present invention to propose an equipment which is simple, reliable, of low production and utilization costs, offering a wide flexibility of adaptation and a high level of safety, while freeing the user from the obligations of counting, and enabling a follow up of compliance with the prescription.

For this purpose, according to a characteristic of the invention, the control device includes program means for controlling sequences of supplying doses to the user as well as, advantageously, means for recording and controlling sequences of effectively supplying doses to the user.

According to a more specific characteristic of the invention, the program control means, as well as, advantageously the recording and control means, include an information carrying support, advantageously a chip bearing card, which can be connected to the control device and, advantageously, to a separate station for programming and reading informations recorded in said information carrying support.

According to the present invention, doses supplied to a user means a gas or a mixture of gases in gaseous form, for example oxygen or oxygen enriched air, carrying solid or liquid particles of a medicinal substance.

It is another object of the present invention to propose a process of operating an equipment as defined above, including the steps of introducing in the program means a total duration of a sequence of supplying doses, as well as, advantageously, at least a given time of the day for the start of a sequence of supplying doses.

BRIEF DESCRIPTION OF DRAWINGS

Other characteristics and advantages of the present invention will appear from the following description of a embodiment, given by way of illustration but without limitation, with reference to the annexed drawing, in which:

the single FIGURE is a schematic illustration of an equipment for programming and controlling the administration of medicinal aerosols according to an embodiment of the invention.

DESCRIPTION OF PREFERRED EMBODIMENT

There is illustrated in the single FIGURE a nebulizer 1 in a circuit 2 between a source of gas 3 and the respiratory tracts of a patient, the nebulizer comprising a separate air inlet 4. Circuit 2 includes, upstream of the nebulizer 1, a device for controlling the supply of doses of carrier gas from source 3 including a three way valve 5 coupled to a sensor 6 which is responsive to the phases of inhalation and exhalation of the user as for example described in the document EP-A-0.183.593. Suffice it to mention here that sensor 6 includes a differential capsule 7 carrying a movable flap 8 which can be selectively disposed in a luminous path between a photodiode 9 and a phototransistor 10 controlling a control loop of the electrovalve 5 including, successively, a shaping circuit 11, a monostable circuit 12 providing a signal for controlling the opening of the electrovalve 5 for a duration which is determined by a duration control circuit 13, and a stage of power outlet 14. Typically, the duration of a nebulization phase should be slightly shorter than the duration of an inhalation. In practice, the duration control circuit 13 could be limited to a selector which selects three control levels: "adult", "child" and "baby".

According to an aspect of the invention, between circuits 11 and 12 a selective locking circuit 15, with transistors, integrated circuits, logic or with relays is disposed, the locking circuit being coupled to a control device which will be described below. Moreover, a counting or display device 16 counts and displays the number of signals of opening of the electrovalve 5 which are controlled by sensor 6.

In the embodiment which is illustrated, the control device comprises a station 17 for reading and writing on an information carrying support C, for example a multitrack magnetic band or, preferably, a chip bearing card with non volatile (SRAM or "Flash") or programmable memory. In reading mode, device 17 provides signals to a device 18 for counting and reading a number of gas puffs delivered by the electrovalve 5 during a gas supplying sequence, and to a device 19 for counting and reading the daily number of sequences of supplying doses of gas, both being connected to a clock 30. Device 18 provides an outlet signal to a device 20 for detecting the end of a sequence which is coupled at the outlet to a non volatile memory 21 whose content may be discharged in the integrated circuit of card C in the writing mode of device 17. Memory 21, as well as device 19, are connected to a device 22 which authorizes the start of sequence which provides at the outlet a signal which, in the same manner as with respect to an outlet signal of device 20, is sent to a logic gate 23 which controls locking circuit 15. As a variant, the control device may also include a circuit 24 for analyzing defects and operating an alarm which receives signals from device 17 and from the outlet of the shaping circuit 11 to provide an outlet signal which is sent to an inlet of circuit 20 for detecting the end of a sequence.

In the embodiment which is illustrated, the equipment is completed by a separate programming and reading station P including a programming and reading device 25 with one microprocessor to which can be connected chip bearing card C, said station being connected to a programming/screen keyboard assembly 26 and to a printer 27. Advantageously, the control chain of the electrovalve 5 is grouped into an independent basic module A, provided with an internal clock (not illustrated), the control device described above being grouped into a control module B which can be associated with the basic module A by means of fast connections and advantageously, in operating mode, getting its electrical energy from a source of electrical power 28 of the basic module A.

The operation of the equipment is as follows:

A specific chip bearing card C (individual transportation information carrying support) is associated with a given patient. Depending on the proposed treatment for the patient, the medical doctor, holder of the programming/reading station P, introduces in the latter card C of the patient and writes down therein an identification code of the patient, the time for taking medications (start of the sequence) and the number of puffs to be taken when taking the medication (duration of the sequence). The card is then given back to the patient who introduces it into the reading/writing device 17 of his control module B which will then place basic module A in a holding position under control, so as to start the operation, and therefore freeing the medicinal aerosol, only at the programmed time which has been fixed by the practitioner. This has a primary interest for chrono-biologically dependent therapies and for antibiotherapy. Similarly, the number of puffs which are released when the patient inhales could not exceed the number which has been preprogrammed by the practitioner. This frees the practitioner and the patient from an error through an excess, since an error by default may be indicated by the alarm triggered by circuit 24, in the case, for example, where the two following conditions are combined: the number of prescribed puffs is not reached and the time spent since the last puff has exceeded a determined duration, particularly one to two minutes.

In addition to its function of providing pre-programmed informations, chip bearing card C permanently records, in device 17, the behavior of the patient and enables for example to verify faults in complying with the prescription of the practitioner as reflected by the program originally designed. Thus, during a consultation, the patient brings back his card C to the medical doctor, who, by introducing it into device 25 of station P, may read, and even obtain a print, thereby verifying the dates, times of sessions truly or incompletely carried out with the value of the non compliance being indicative of a number of lacking puffs. Indeed, in case of a therapeutic failure, the question of observance is of primary importance: this is why reading the informations recorded on the chip bearing card enables the medical doctor to determine compliance or non-compliance with his prescription.

Although the present invention has been described with reference to a specific embodiment, it is not limited thereto but, on the contrary, it is capable of modifications and variants which will be obvious to one skilled in the art. In particular, the equipment according to the invention may be used for a large number of apparatuses for home care, for example the programming the release of a ventilation CPAP so as not to be interfered by its operation when falling asleep, to monitor the observance as well as the quality of its control, or even to monitor or control the number of uses of an oxygen concentrator and the monitoring of the concentration in oxygen which is released.

We claim:

1. A system for supplying to a respiratory tract of a user a plurality of discrete puffs of at least one gas, each of the puffs containing particles of at least one active product; the system comprising:

a nebulizer containing the particles of the active product, the nebulizer being in a gas circuit between a source of the gas and the user;

gas flow control means for delivering in each of the puffs a metered amount of the gas to the nebulizer and to the user;

sensing means for sensing a breath phase of the user, for initiating each of the puffs in response to the breath phase of the user, and for counting the puffs;

sequence-control programmable means, operatively coupled to the sensing means, for controlling operations of the gas flow control means and delivering a plurality of the puffs in a predetermined sequence of the puffs to the user, the predetermined sequence being delivered according to a puff sequence program, the puff sequence program including a maximum number of puffs;

a transportable memory storage unit for transporting the puff sequence program;

read/write record means for the sequence-control programmable means to accept the puff sequence program from the memory storage unit and for recording timing parameters of the sequence of the puffs on the memory storage unit; and a programing station for entering the puff sequence program onto the memory storage unit.

2. The system according to claim 1, wherein the memory storage unit includes a chip.

3. The system according to claim 1, wherein the memory storage unit includes a magnetic card.

4. The system according to claim 1, wherein the sequence-control programmable means includes recording means for recording user record data on the memory storage unit.

5. The system according to claim 4, wherein the user record data includes selectively a dosage time, a dosage puff number of puffs accepted by the user, and a dosage date.

6. The system according to claim 4, wherein the station includes means for displaying the user record data.

7. The system according to claim 1, wherein the sequence-control programmable means includes means for controlling a total duration of supplying doses during each sequence.

8. The system according to claim 1, comprising an alarm.

9. A method of supplying to a respiratory tract of a user a plurality of discrete puffs of at least one gas, each of the puffs containing particles of at least one active product, comprising the steps of:

providing a nebulizer containing the particles of the active product, the nebulizer being in a gas circuit between a source of the gas and the user;

providing gas flow control means for delivering in each of the puffs a metered amount of the gas to the nebulizer and to the user;

providing sensing means for sensing a breath phase of the user, for initiating each of the puffs in response to the breath phase of the user such that each puff corresponds to one breath of the user, and for counting the puffs;

providing sequence-control programmable means, operatively coupled to the sensing means, for controlling operations of the gas flow control means and delivering a plurality of the puffs in a predetermined sequence of the puffs to the user, the predetermined sequence being delivered according to a puff sequence program, the puff sequence program including a maximum number of puffs;

providing a transportable memory storage unit for transporting the puff sequence program;

providing read/write record means for the sequence-control means to accept the puff sequence program from the memory storage unit and for recording timing parameters of the sequence of the puffs on the memory storage unit; and providing a programming station for entering the puff sequence program onto the memory storage unit;

programming puff sequence data, including a maximum number of the puffs, onto the memory storage unit at the station;

transferring the memory storage unit to the sequence-control means; and administering the puffs to the user according to the puff sequence data.

10. The method according to claim 9, wherein the puff sequence data includes at least one predetermined beginning time of the predetermined sequence of puffs.

11. The method according to claim 9, wherein the puff sequence data includes user identification.

12. The method according to claim 9, comprising a step of providing recording means, of the sequence-control means, for recording on the memory storage unit selectively a dosage time, a dosage puff number, and a dosage date.

13. The method according to claim 9, comprising a step of providing means for displaying a number of doses supplied to the user during a sequence.

* * * * *